(12) United States Patent
Yoshida et al.

(10) Patent No.: US 11,198,005 B2
(45) Date of Patent: Dec. 14, 2021

(54) METHODS AND SYSTEMS FOR BLOCKING NERVE ACTIVITY PROPAGATION IN NERVE FIBERS

(71) Applicant: Indiana University Research and Technology Corporation, Indianapolis, IN (US)

(72) Inventors: Ken Yoshida, Carmel, IN (US); Michael Ryne Horn, Indianapolis, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 97 days.

(21) Appl. No.: 16/606,301

(22) PCT Filed: Apr. 19, 2018

(86) PCT No.: PCT/US2018/028403
§ 371 (c)(1),
(2) Date: Oct. 18, 2019

(87) PCT Pub. No.: WO2018/195332
PCT Pub. Date: Oct. 25, 2018

(65) Prior Publication Data
US 2020/0129767 A1  Apr. 30, 2020

Related U.S. Application Data

(60) Provisional application No. 62/487,264, filed on Apr. 19, 2017.

(51) Int. Cl.
*A61N 1/36* (2006.01)

(52) U.S. Cl.
CPC ..... *A61N 1/36157* (2013.01); *A61N 1/36135* (2013.01); *A61N 1/36171* (2013.01)

(58) Field of Classification Search
CPC ............ A61N 1/36057; A61N 1/36071; A61N 1/36157; A61N 1/36171
See application file for complete search history.

(56) References Cited

U.S. PATENT DOCUMENTS 8,731,676 B2   5/2014  Fang
RE45,718 E    10/2015  Kilgore
(Continued)

FOREIGN PATENT DOCUMENTS

WO   WO 2007/082382   7/2007
WO   WO 2018/195332  10/2018

OTHER PUBLICATIONS

D. T. Simon, K. C. Larsson, D. Nilsson, G. Burström, G. Galter, M. Berggren, and A. Richter-Dahlfors, "An organic electronic biomimetic neuron enables auto-regulated neuromodulation," *Biosens Bioelectron*, vol. 71, pp. 359-364.
(Continued)

*Primary Examiner* — Allen Porter
(74) *Attorney, Agent, or Firm* — Faegre Drinker Biddle & Reath LLP (57) ABSTRACT

A nerve activity blocking system (100) includes a blocking electrode (102) configured to generate a blocking electrical signal that blocks, at least in part, an action potential propagating through a nerve system of a body. using a low frequency alternating current. The blocking electrical signal prevents propagation of the action potential by overriding another electrical signal controlling an organ of the body.

12 Claims, 6 Drawing Sheets

(56) References Cited

U.S. PATENT DOCUMENTS

| | | | |
|---|---|---|---|
| 9,295,841 B2 | 3/2016 | Fang | |
| 2004/0127953 A1 | 7/2004 | Kilgore | |
| 2005/0102007 A1 | 5/2005 | Ayal | |
| 2005/0131485 A1* | 6/2005 | Knudson | A61N 1/321 607/40 |
| 2011/0071590 A1* | 3/2011 | Mounaim | A61N 1/36171 607/41 |
| 2011/0125216 A1* | 5/2011 | Kilgore | A61N 1/0556 607/46 |
| 2012/0016448 A1* | 1/2012 | Lee | A61N 1/36171 607/72 |
| 2015/0182749 A1 | 7/2015 | Fang | |
| 2016/0121120 A1 | 5/2016 | Tweden | |
| 2017/0050024 A1* | 2/2017 | Bhadra | A61N 1/36062 |
| 2017/0246453 A1 | 8/2017 | Fang | |

OTHER PUBLICATIONS

ALoysio Luigi Galvani (1737-1798) "Discoverer of animal electricity," *JAMA*, vol. 201, No. 8, pp. 626-627.

R. N. Doshi, T.-J. Wu, M. Yashima, Y.-H. Kim, J. J. C. Ong, J.-M. Cao, C. Hwang, P. Yashar, M. C. Fishbein, H. S. Karagueuzian, and P.-S. Chen, "Relation between ligament of Marshall and Adrenergic atrial tachyarrhythmia," *Circulation*, vol. 100, No. 8, p. 876-883.

A. Y. Tan, "Electrical connections between left superior pulmonary vein, left atrium, and ligament of Marshall: implications for mechanisms of atrial fibrillation," *AJP: Heart and Circulatory Physiology*, vol. 290, No. 1, pp. H312-H322.

J. Lin, B. J. Scherlag, Z. Lu, Y. Zhang, S. Liu, E. Patterson, W. M. Jackman, R. Lazzara, and S. S. Po, "Inducibility of atrial and ventricular arrhythmias along the ligament of Marshall: Role of autonomic factors," *Journal of Cardiovascular Electrophysiology*, vol. 19, No. 9, p. 955-962.

M. Makino, S. Inoue, T.-A. Matsuyama, G. Ogawa, T. Sakai, Y.I. Kobayashi, T. Katagiri, and H. Ota, "Diverse myocardial extension and autonomic innervation on ligament of Marshall in humans," *Journal of Cardiovascular Electrophysiology*, vol. 17, No. 6, p. 594-599.

T.-J. Wu, J. J. C. Ong, C.-M. Chang, R. N. Doshi, M. Yashima, H.-L. A. Huang, M. C. Fishbein, C.-T. Ting, H. S. Karagueuzian, and P.-S. Chen, "Pulmonary veins and ligament of Marshall as sources of rapid activations in a canine model of sustained atrial fibrillation," *Circulation*, vol. 103, No. 8, p. 1157-1163.

D. Katritsis, J. P. Ioannidis, C. E. Anagnostopoulos, G. E. Sarris, E. Giazitzoglou, S. Korovesis, and A. J. Camm, "Identification and catheter ablation of extracardiac and intracardiac components of ligament of Marshall tissue for treatment of paroxysmal atrial fibrillation," *J. Cardiovasc. Electrophysiology.*, vol. 12, No. 7, p. 750-758.

C. Hwang and P.-S. Chen, "Ligament of Marshall: Why it is important for atrial fibrillation ablation," *Heart Rhythm*, vol. 6, No. 12, pp. S35-S40.

M. Maruyama, T. Ino, S. Miyamoto, T. Tadera, H. Atarashi, and H. Kishida, "Characteristics of the electrical activity within the persistent left superior vena cava: Comparative view with reference to the ligament of Marshall," *Journal of Electrocardiology*, vol. 36, No. 1, pp. 53-57.

D. T. Kim, A. C. Lai, C. Hwang, L.-T. Fan, H. S. Karagucuzian, P.-S. Chen, and M. C. Fishbein, "The ligament of Marshall: a structural analysis in human hearts with implications for atrial arrhythmias," *Journal of the American College of Cardiology*, vol. 36, No. 4, pp. 1324-1327.

J. Lin, B. J. Scherlag, G. Niu, Z. Lu, E. Patterson, S. Liu, R. Lazzara, W. M. Jackman, and S. S. Po, "Autonomic elements within the ligament of Marshall and inferior left ganglionated plexus mediate functions of the atrial neural network," *Journal of Cardiovascular Electrophysiology*, vol. 20, No. 3, pp. 318-324.

J. Marshall, "On the development of the great anterior veins in man andMammalia; including an account of certain remnants of Foetal structure found in the adult, a comparative view of these great veins in the different Mammalia, and an analysis of their occasional peculiarities in the human subject," *Phil. Trans. R. Soc. Lond.*, vol. 140, pp. 133-170.

E. Vanoli, G. M. D. Ferrari, M. Stramba-Badiale, S. S. Hull, R. D. Foreman, and P.J. Schwartz, "Vagal stimulation and prevention of sudden death in conscious dogs with a healed myocardial infarction." *Circulation Research*, vol. 68, No. 5, pp. 1471-1481.

M. Tosato, K. Yoshida, E. Toft, V.Nekrasas, and J. J. Struijk, "Closed-loop control of the heart rate by electrical stimulation of the vagus nerve," *Med Biol Eng Comput*, vol. 44, No. 3, pp. 161-169.

M. Tosato, K. Yoshida, E. Toft, and J. J. Struijk, "Quasi-trapezoidal pulses to selectively block the activation of intrinsic laryngeal muscles during vagal nerve stimulation," *J. Neural Eng.*, vol. 4, No. 3, p. 205.

P. J. Schwartz, G. M. De Ferrari, A. Sanzo, M. Landolina, R. Rordorf, C. Raineri, C. Campana, M. Revera, N. Ajmone-Marsan, L. Tavazzi, and A. Odero, "Long term vagal stimulation in patients with advanced heart failure first experience in man," *European Journal of Heart Failure*, vol. 10, No. 9, pp. 884-891.

S. Li, B. J. Scherlag, L. Yu, X. Sheng, Y. Zhang, R. Ali, Y. Dong, M. Ghias, and S. S. Po, "Low-level Vagosympathetic stimulation a paradox and potential new modality for the treatment of focal atrial fibrillation," *Circ Arrhythm Electrophysiol*, vol. 2, No. 6, pp. 645-651.

E. Beaumont, G. L. Wright, E. M. Southerland, Y. Li, R. Chui, B. H. Ken Knight, J. A. Armour, and J. L. Ardell, "Vagus nerve stimulation mitigates intrinsic cardiac neuronal remodeling and cardiac hypertrophy induced by chronic pressure overload in guinea pig," *American Journal of Physiology—Heart and Circulatory Physiology*, vol. 310, No. 10, pp. H1349 H1359.

K. Nakamura, O. A. Ajijola, E. Aliotta, J. A. Armour, J. L. Ardell, and K. Shivkumar, "Pathological effects of chronic myocardial infarction on peripheral neurons mediating cardiac neurotransmission," *Autonomic Neuroscience*, vol. 197, pp. 34-40.

J. S. Ulphani, R. Arora, J. H. Cain, R. Villuendas, S. Shen, D. Gordon, F. Inderyas, L. A. Harvey, A. Morris, J. J. Goldberger, and A. H. Kadish, "The ligament of Marshall as a parasympathetic conduit," *American Journal of Physiology Heart and Circulatory Physiology*, vol. 293, No. 3, pp. H1629-H1635.

R. Arora, J. S. Ulphani, R. Villuendas, J. Ng, L. Harvey, S. Thordson, F. Inderyas, Y.Lu, D. Gordon, P.Denes, R. Greene, S. Crawford, R. Decker, A. Morris, J. Goldberger, and A. H. Kadish, "Neural substrate for atrial fibrillation: implications for targeted parasympathetic blockade in the posterior left atrium," *American Journal of Physiology—Heart and Circulatory Physiology*, vol. 294, No. 1, pp. H134-H144.

F. A. Koopman, S. S. Chavan, S. Miljko, S. Grazio, S. Sokolovic, P.R. Schuurman, A. D. Mehta, Y.A. Levine, M. Faltys, R. Zitnik, K. J. Tracey, and P.P. Tak, "Vagus nerve stimulation inhibits cytokine production and attenuates disease severity in rheumatoid arthritis," *Proc Natl Acad Sci U S A*, vol. 113, No. 29, pp. 8284-8289.

A. Onda, S. Uchida, H. Suzuki, and H. Hotta, "Stimulus frequency-dependent inhibition of micturition contractions of the urinary bladder by electrical stimulation of afferent a, a, and c fibers in cutaneous branches of the pudendal nerve," *J Physiol Sci*, p. 1-6.

T. Fulop and C. Smith, "Matching native electrical stimulation by graded chemical stimulation in isolated mouse adrenal chromaffin cells," *J Neurosei Methods*, vol. 166, No. 2, p. 195-202.

W. Jensen, S. Micera, X. Navarro, T. Stieglitz, D. Guiraud, J. Divoux, P.Rossini, and K. Yoshida, "Development of an implantable transverse intrafascicular multichannel electrode (TIME) system for relieving phantom limb pain," in *2010 Annual International Conference of the IEEE Engineering in Medicine and BiologySociety (EMBC)*, pp. 6214-6217.

T.Boretius, J. Badia, A. Pascual-Font, M. Schuettler, X. Navarro, K. Yoshida, and T. Stieglitz, "A transverse intrafascicular multichannel electrode ( TIME) to interface with the peripheral nerve," *Biosensors and Bioelectronics*, vol. 26, No. 1, p. 62-69.

J. A. Mahnstrom, T.G. McNaughton, and K. W. Horch, "Recording properties and biocompatibility of chronically implanted polymer-based intrafascicular electrodes," *Ann Biomed Eng*, vol. 26, No. 6, pp. 1055-1064.

(56) References Cited

OTHER PUBLICATIONS

Z. Lertmanorat and D. M. Durand, "Extracellular voltage profile for reversing the recruitment order of peripheral nerve stimulation: a simulation study," *J. Neural Eng.*, vol. 1, No. 4, p. 202.

A. Ranieri, R. E. Andersen, M. V.Lauridsen, and K. R. Harreby, "A combined interfascicular-cuff electrode (ICE) for selective recruitment of polyfascicular peripheral nerves using transversal stimulation," in *Replace, Repair, Restore, Relieve Bridging Clinical and Engineering Solutions in Neurorehabilitation*, ser. Biosystems & Biorobotics, W. Jensen, O. K. Andersen, and M. Akay, Eds. Springer International Publishing, No. 7, p. 685-694.

S. Qiao and K. Yoshida, "Influence of unit distance and conduction velocity on the spectra of extracellular action potentials recorded with intrafascicular electrodes," *Med Eng Phys*, vol. 35, No. 1, pp. 116-124.

M. Schiefer, R. Triolo, and D. Tyler, "A model of selective activation of the femoral nerve with a flat interface nerve electrode for a lower extremity neuroprosthesis," *IEEE Transactions on Neural Systems and Rehabilitation Engineering*, vol. 16, No. 2, p. 195-204.

N. Lago, K. Yoshida, K. P.Koch, and X. Navarro, "Assessment of biocompatibility of chronically implanted polyimide and platinum intrafascicular electrodes," *IEEE Trans Biomed Eng*, vol. 54, No. 2, pp. 281-290.

K. Yoshida, K. Hennings, and S. Kammer, "Acute performance of the thin-film longitudinal intra-fascicular electrode," in *The First IEEE/RAS-EMBSInternational Conference on Biomedical Robotics and Biomechatronics, 2006. BioRob 2006*, pp. 296-300.

S. Qiao, T. Stieglitz, and K. Yoshida, "Estimation of the electrode-fiber bioelectrical coupling from extracellularly recorded single fiber action potentials," *IEEE Transactions on Neural Systems and Rehabilitation Engineering*, vol. PP, No. 99, pp. 1-1.

M. Horn, S. Qiao, and K. Yoshida, "Effect of the nerve fiber path eccentricity on the single fiber action potential," in *2013 6th International IEEE/EMBS Conference on Neural Engineering (NER)*, pp. 1139-1142.

E.-K. Choi, M. J. Shen, S. Han, D. Kim, S. Hwang, S. Sayfo, G. Piccirillo, K. Frick, M. C. Fishbein, C. Hwang, S.-F. Lin, and P.-S. Chen, "Intrinsic cardiac nerve activity and paroxysmal atrial tachyarrhythmia in ambulatory dogs," *Circulation*, vol. 121, No. 24, pp. 2615-2623.

B.-Y. Li, G.-F. Qiao, B. Feng, R.-B. Zhao, Y.-J. Lu, and J. H. Schild, "Electrophysiological and neuroanatomical evidence of sexual dimorphism in aortic baroreceptor and vagal afferents in rat," *Am J Physiol Regul Integr Comp Physiol*, vol. 295, No. 4, pp. RI301-R1310.

H. Helmholtz, "Ueber einige Gesetze der Vertheilung elektrischer ströme in körperlichen leitern, mit Anwendung auf die thierisch-elektrischen Versuche (schluss.)," *Ann. Phys.*, vol. 165, No. 7, pp. 353-377.

W. A. H. Rushton, "The effect upon the threshold for nervous excitation of the length of nerve exposed, and the angle between current and nerve," *The Journal of Physiology*, vol. 63, No. 4, pp. 357-377.

"A physical analysis of the relation between threshold and interpolar length in the electric excitation of medullated nerve," *The Journal of Physiology*, vol. 82, No. 3, p. 332-352.

"Action potentials from the isolated nerve cord of the earthworm," *Proceedings of the Royal Society of London B: Biological Sciences*, vol. 132, No. 869, p. 423-437.

"Reflex conduction in the giant fibres of the earthworm," *Proceedings of the Royal Society of London B: Biological Sciences*, vol. 133, No. 870, p. 109-120.

"A theory of the effects of fibre size in medullated nerve," *The Journal of Physiology*, vol. 115, No. 1, pp. 101-122.

J. H. Schild, J. W. Clark, M. Hay, D. Mendelowitz, M. C. Andresen, and D. L. Kunze, "A- and c-type rat nodose sensory neurons: model interpretations of dynamic discharge characteristics," *Journal of Neurophysiology*, vol. 71, No. 6, pp. 2338-2358.

J. H. Schild and D. L. Kunze, "Experimental and modeling study of Na+ current heterogeneity in rat nodose neurons and its impact on neuronal discharge," *Journal of Neurophysiology*, vol. 78, No. 6, pp. 3198-3209.

R. Plonsey, "The active fiber in a volume conductor," *IEEE Transactions on Biomedical Engineering*, vol. BME-21, No. 5, pp. 371-381.

J. J. Struijk, "The extracellular potential of a myelinated nerve fiber in an unbounded medium and in nerve cuff models." *Biophys J*, vol. 72, No. 6, pp. 2457-2469.

A. L. Hodgkin and A. F. Huxley, "A quantitative description of membrane current and its application to conduction and excitation in nerve," *J Physiol*, vol. 117, No. 4, pp. 500-544.

P.A. Glazebrook, A. N. Ramirez, J. H. Schild, C.-C. Shieh, T. Doan, B. A. Wible, and D. L. Kunze, "Potassium channels kv1.1, kv1.2 and kv1.6 influence excitability of rat visceral sensory neurons," *J Physiol*, vol. 541, pp. 467-482.

J. T. Rubinstein, "Analytical theory for extracellular electrical stimulation of nerve with focal electrodes. II. passive myelinated axon." *Biophys J*, vol. 60, No. 3, p. 538-555.

P. Einziger, L. Livshitz, and J. Mizrahi, "Generalized cable equation model for myelinated nerve fiber," *IEEE Transactions on Biomedical Engineering*, vol. 52, No. 10, p. 1632-1642.

N. Ganapathy and J. W. Clark, "Extracellular currents and potentials of the active myelinated nerve fiber." *Biophys J*, vol. 52, No. 5, p. 749-761.

A. R. Brazhe, G. V. Maksimov, E. Mosekilde, and O. V. Sosnovtseva, "Excitation block in a nerve fibre model owing to potassium-dependent changes in myelin resistance," *Interface Focus*, vol. 1, No. 1, pp. 86-100.

J. H. Frijns, J. Mooij, and J. H. ten Kate, "A quantitative approach to modeling mammalian myelinated nerve fibers for electrical prosthesis design," *IEEE Trans Biomed Eng*, vol. 41, No. 6, pp. 556-566.

S. Severi, M. Fantini, L. A. Charawi, and D. DiFrancesco, "An updated computational model of rabbit sinoatrial action potential to investigate the mechanisms of heart rate modulation," *J. Physiol. (Lond.)*, vol. 590, p. 4483-4499.

J. E. Smit, T. Hanekom, and J. J. Hanekom, "Modelled temperature-dependent excitability behaviour of a generalised human peripheral sensory nerve fibre," *Biol Cybern*, vol. 101, No. 2, p. 115-130.

V. Schnabel and J. Struijk, "Evaluation of the cable model for electrical stimulation of unmyelinated nerve fibers," *IEEE Transactions on Biomedical Engineering*, vol. 48, No. 9, pp. 1027-1033.

J. Struijk, J. Holsheimer, G. van der Heide, and H. B. K. Boom, "Recruitment of dorsal column fibers in spinal cord stimulation: influence of collateral branching," *IEEE Transactions on Biomedical Engineering*, vol. 39, No. 9, pp. 903-912.

C. C. McIntyre, A. G. Richardson, and W. M. Grill, "Modeling the excitability of mammalian nerve fibers: influence of afterpotentials on the recovery cycle," *J. Neurophysiol.*, vol. 87, No. 2, pp. 995-1006.

S. G. Waxman and J. M. Ritchie, "Organization of ion channels in the myelinated nerve fiber," *Science*, vol. 228, No. 4707, pp. 1502-1507.

S. Y. Chiu and W. Schwarz, "Sodium and potassium currents in acutely demyelinated internodes of rabbit sciatic nerves," *J. Physiol. (Lond.)*, vol. 391, p. 631-649.

C. C. McIntyre and W. M. Grill, "Extracellular stimulation of central neurons: influence of stimulus waveform and frequency on neuronal output," *J. Neurophysiol.*, vol. 88, No. 4, pp. 1592-1604.

S. G. Waxman and J. M. Ritchie, "Molecular dissection of the myelinated axon,"*Ann Neurol.*, vol. 33, No. 2, pp. 121-136.

M. S. Malagodi, K. W. Horch, and A. A. Schoenberg, "An intrafascicular electrode for recording of action potentials in peripheral nerves," *Ann Biomed Eng*, vol. 17, No. 4, p. 397-410.

T.G. McNaughton and K. W. Horch, "Metallized polymer fibers as leadwires and intrafascicular microelectrodes," *J. Neurosci. Methods*, vol. 70, No. 1, p. 103-110.

S. Micera, X. Navarro, J. Carpaneto, L. Citi, O. Tonet, P.M. Rossini, M. C. Carrozza, K. P. Hoffmann, M. Viv, K. Yoshida, and P. Dario, "On the use of longitudinal intrafascicular peripheral interfaces for (56) References Cited

OTHER PUBLICATIONS the control of cybernetic hand prostheses in amputees," *IEEE Trans Neural Syst Rehabil Eng*, vol. 16, No. 5, p. 453-472.
G. David, J. N. Barrett, and E. F. Barrett, "Activation of internodal potassium conductance in rat myelinated axons." *J Physiol*, vol. 472, p. 177-202.
S. Y. Chiu and J. M. Ritchie, "Evidence for the presence of potassium channels in the paranodal region of acutely demyelinated mammalian single nerve fibres." *J Physiol*, vol. 313, pp. 415-437.
J. R. Howe and J. M. Ritchie, "Sodium currents in Schwann cells from myelinated and non-myelinated nerves of neonatal and adult rabbits." *J Physiol*, vol. 425, pp. 169-210.
S. Colilla, A. Crow, W. Petkun, D. E. Singer, T. Simon, and X. Liu, "Estimates of current and future incidence and prevalence of atrial fibrillation in the U.S. adult population," *The American Journal of Cardiology*, vol. 112, No. 8, pp. 1142-1147.
A. M. Rush, M. E. Bru, A. A. Elliott, and J. R. Elliott, "Electrophysiological properties of sodium current subtypes in small cells from adult rat dorsal root ganglia," *J. Physiol. (Lond.)*, vol. 511 (Pt 3), pp. 771-789.
W. Rall, "Core conductor theory and cable properties of neurons," in *Comprehensive Physiology*. John Wiley & Sons, Inc.
A. F. Huxley and R. Stämpfli, "Evidence for saltatory conduction in peripheral myelinated nerve fibres," *J Physiol*, vol. 108, No. 3, pp. 315-339.
V.P.S. Fazan, H. C. Salgado, and A. A. Barreira, "Aortic depressor nerve myelinated fibers in acute and chronic experimental diabetes," *Am J Hypertens*, vol. 19, No. 2, pp. 153-160.
T. Chomiak and B. Hu, "What is the optimal value of the g-ratio for myelinated fibers in the rat CNS? a theoretical approach," *PLoS One*, vol. 4, No. 11.
L. Nez, L. Senovilla, S. Sanz-Blasco, P. Chamero, M. T. Alonso, C. Villalobos, and J. Garca-Sancho, "Bioluminescence imaging of mitochondrial Ca2+ dynamics in soma and neurites of individual adult mouse sympathetic neurons," *J Physiol*, vol. 580, pp. 385-395.
D. Zenisek and G. Matthews, "The role of mitochondria in presynaptic calcium handling at a ribbon synapse," *Neuron*, vol. 25, No. 1, pp. 229-237.
J. R. Huguenard, D. A. Coulter, and D. A. Prince, "A fast transient potassium current in thalamic relay neurons: kinetics of activation and inactivation," *Journal of Neurophysiology*, vol. 66, No. 4, pp. 1304-1315.
J. R. Schwarz, "The effect of temperature on Na currents in rat myelinated nerve fibres," *Pflügers Arch.*, vol. 406, No. 4, pp. 397-404.

D. Yamamoto and N. Suzuki, "Characterization of single non-inactivating potassium channels in primary neuronal cultures of *Drosophila*," *Journal of Experimental Biology*, vol. 145, No. 1, pp. 173-184.
J. Clark and R. Plonsey, "The extracellular potential field of the single active nerve fiber in a volume conductor," *Biophys J*, vol. 8, No. 7, pp. 842-864.
K. Yoshida, D. Pellinen, D. Pivin, P. Rousche, and D. Kipke, "Development of the thin-film longitudinal intra-fascicular electrode, in *Proceedings, 5th Annual Conference of the International Functional Electrical Stimulation Society, 6th Triennial Conference Neural Prostheses: Motor Systems*", pp. 279-281.
C. Hwang, H. S. Karagueuzian, and P.-S. Chen, "Idiopathic paroxysmal atrial fibrillation induced by a focal discharge mechanism in the left superior pulmonary vein," *Journal of cardiovascular electrophysiology*, vol. 10, No. 5, pp. 636-648.
X. He, Y. Zhou, Y. Chen, L. Wu, Y. Huang, and J. He, "Left atrial posterior wall isolation reduces the recurrence of atrial fibrillation: a meta-analysis," *J Interv Card Electrophysiol*, pp. 1-8.
Y. Sha, B. J. Scherlag, L. Yu, X. Sheng, W. M. Jackman, R. Lazzara, and S. S. Po, "Low-level right vagal stimulation: Anticholinergic and antiadrenergic effects," *Journal of Cardiovascular Electrophysiology*, vol. 22, No. 10, pp. 1147-1153.
G. M. D. Ferrari, H. J. G. M. Crijns, M. Borggrefe, G. Milasinovic, J. Smid, M. Zabel, A. Gavazzi, A. Sanzo, R. Dennert, J. Kuschyk, S. Raspopovic, H. Klein, K. Swedberg, and P.J. Schwartz, "Chronic vagus nerve stimulation: a new and promising therapeutic approach for chronic heart failure," *Eur Heart J*, vol. 32, No. 7, pp. 847-855.
G. C. S. C. Chavez, B.-Y. Li, P. A. Glazebrook, D. L. Kunze, and J. H. Schild, "An afferent explanation for sexual dimorphism in the aortic baroreflex of rat," *American Journal of Physiology—Heart and Circulatory Physiology*, vol. 307, No. 6, pp. H910-H921.
Y. Grinberg, M. Schiefer, D. Tyler, and K. Gustafson, "Fascicular perineurium thickness, size, and position affect model predictions of neural excitation," *IEEE Transactions on Neural Systems and Rehabilitation Engineering*, vol. 16, No. 6, pp. 572-581.
M. R. Horn, "Effect of nerve fiber path eccentricity on the single fiber action potential," *IUPUI 2nd Annual BMEGSA Symposium*.
Written Opinion of the International Searching Authority, dated Jul. 3, 2018, for International Patent Application No. PCT/US2018/028403; 4 pages.
International Search Report issued by the International Searching Authority, dated Jul. 3, 2018, for International Patent Application No. PCT/US2018/028403; 2 pages.

* cited by examiner

METHODS AND SYSTEMS FOR BLOCKING NERVE ACTIVITY PROPAGATION IN NERVE FIBERS

CROSS-REFERENCE

The present application is a national stage entry of International (PCT) Patent Application No. PCT/US2018/028403, filed Apr. 19, 2018, which in turns claims the benefit of U.S. Provisional Application Ser. No. 62/487,264, filed on Apr. 19, 2017, titled "METHODS AND SYSTEMS FOR BLOCKING NERVE ACTIVITY PROPAGATION IN NERVE FIBERS," the disclosure of which is expressly incorporated by reference herein.

FIELD OF THE DISCLOSURE

The present disclosure generally relates to nerve fiber control systems, and more particularly, to methods and systems for blocking nerve activity propagation in nerve fibers of a nervous system.

BACKGROUND OF THE DISCLOSURE

Activity of major organs including kidneys, pancreas, liver, ovaries, spleen, heart, are controlled by a part of a nervous system called an autonomic nervous system. Sensors embedded throughout a body, communicating via the autonomic nervous system, help regulate how these organs function. However, in cases of a chronic disease, the regulation of one or more of these organs is often uncontrollable, due to the disease altering sensory information or control signals to a corresponding organ. In many cases, the illness alters the signals from the sensors regulating the organ, or the signal driving the organ function is excessively high as a result of the illness.

Electrical stimulation applied through indwelling electrodes is seen as a method to reduce these excessively high signals through blocking. For example, an amount of blocking can be adjusted or turned off, and thus the blocking is considered as a tunable and reversible technique to treat the illness. Electrical stimulation can target specific nerve branches implicated in the illness, and thus, unlike drug-based therapies, which circulate an active agent throughout the body, electrical stimulation is specific to a certain region of the body. Current diseases or pathologies where the blocking method is being investigated as a therapy include polycystic ovarian syndrome, diabetes (Type 1 and Type 2), hypertension, asthma, immuno-inflammation, septic shock, and metabolic disorders.

Many of these diseases can be treated surgically by cutting the nerves innervating specific organs. However, surgical interventions are invasive and frequently result in non-reversible side effects. Thus, it is desirable to develop improved treatment methods and systems that provide a non-invasive or reversible intervention to avoid the foregoing problems with existing systems.

SUMMARY

In an embodiment of the present disclosure, a nerve activity blocking system is provided. Included in the nerve activity blocking system is a blocking electrode configured to generate a blocking electrical signal that blocks, at least in part, an action potential propagating through a nerve system of a body, using a low frequency alternating current. The blocking electrical signal prevents propagation of the action potential by overriding another electrical signal controlling an organ of the body.

In one example, a current level of the low frequency alternating current is approximately 100 microampere.

In another example, a frequency level of the low frequency alternating current ranges between 0.01 hertz and 100 hertz.

In yet another example, at least one of frequency and amplitude of the blocking electrical signal selectively controls an effect of the blocking based on a fiber type of the nerve system.

In still another example, the nerve activity blocking system includes a first recording electrode disposed upstream of the blocking electrode, and configured to monitor the action potential propagating through the nerve system.

In yet still another example, the nerve activity blocking system includes a second recording electrode disposed downstream of the blocking electrode and configured to monitor an extent of blocking of the action potential by the blocking electrical signal.

In a further example, the blocking electrical signal includes at least one non-blocking zone and at least one blocking zone. Each zone is defined based on a voltage range associated with the blocking electrode. In a variation, while the at least one non-blocking zone continues, the blocking electrical signal allows the action potential to pass until a voltage level delivered to the blocking electrode reaches a first predetermined threshold. In another variation, while the at least one blocking zone continues, the blocking electrical signal blocks the action potential until a voltage level delivered to the blocking electrode reaches a second predetermined threshold.

In a yet further example, the nerve activity blocking system includes another blocking electrode configured to generate an electrical signal that causes a complete block of the action potential by phasing the electrical signal with the blocking electrical signal.

In a still further example, the blocking electrode is operating at a frequency outside of a recording bandwidth of nerve activity in the body.

In another embodiment of the present disclosure, a method of blocking a nerve activity in a body is disclosed. The method includes generating, using a blocking electrode, a blocking electrical signal that blocks, at least in part, an action potential propagating through a nerve system of the body using a low frequency alternating current, and preventing, using the blocking electrical signal, propagation of the action potential by overriding another electrical signal controlling an organ of the body.

In one example, the method further includes setting a current level of the low frequency alternating current at approximately 100 microampere.

In another example, the method further includes setting a frequency level of the low frequency alternating current ranging between 0.01 hertz and 100 hertz.

In yet another example, the method further includes selectively controlling an effect of the blocking based on a fiber type of the nerve system based on at least one of frequency and amplitude of the blocking electrical signal.

In still another example, the method further includes disposing a first recording electrode upstream of the blocking electrode, and monitoring the action potential propagating through the nerve system using the first recording electrode.

In yet still another example, the method further includes disposing a second recording electrode downstream of the blocking electrode, and monitoring an extent of blocking of the action potential by the blocking electrical signal using the second recording electrode.

In a further example, the method further includes including, in the blocking electrical signal, at least one non-blocking zone and at least one blocking zone, wherein each zone is defined based on a voltage range associated with the blocking electrode. The method further includes allowing, while the at least one non-blocking zone continues, the action potential to pass until a voltage level delivered to the blocking electrode reaches a first predetermined threshold, and blocking, while the at least one blocking zone continues, the action potential until the voltage level delivered to the blocking electrode reaches a second predetermined threshold.

In a yet further example, the method further includes generating, using another blocking electrode, an electrical signal that causes a complete block of the action potential by phasing the electrical signal with the blocking electrical signal.

In a still further example, the method further includes operating the blocking electrode at a frequency outside of a recording bandwidth of nerve activity in the body.

Additional features and advantages of the present disclosure will become apparent to those skilled in the art upon consideration of the following detailed description of the illustrative embodiment exemplifying the best mode of carrying out the present disclosure as presently perceived.

BRIEF DESCRIPTION OF THE DRAWINGS

The features and advantages of the disclosure will become more readily appreciated as the same become better understood by reference to the following detailed description when taken in conjunction with the accompanying drawings, where.

While the present disclosure is amenable to various modifications and alternative forms, specific embodiments have been shown by way of example in the drawings and are described in detail below. The intention, however, is not to limit the present disclosure to the particular embodiments described. On the contrary, the present disclosure is intended to cover all modifications, equivalents, and alternatives falling within the scope of the present disclosure as defined by the appended claims.

DETAILED DESCRIPTION OF EMBODIMENTS

For the purpose of promoting an understanding of the principles of the present disclosure, reference will now be made to the embodiments illustrated in the drawings, which are described below. The embodiments disclosed below are not intended to be exhaustive or limit the present disclosure to the precise form disclosed in the following detailed description. Rather, the embodiments are chosen and described so that others skilled in the art may utilize their teachings. It will be understood that no limitation of the scope of the present disclosure is thereby intended. The present disclosure includes any alterations and further modifications in the illustrated devices and described methods and further applications of the principles of the present disclosure which would normally occur to one skilled in the art to which the present disclosure relates.

Figure 1:
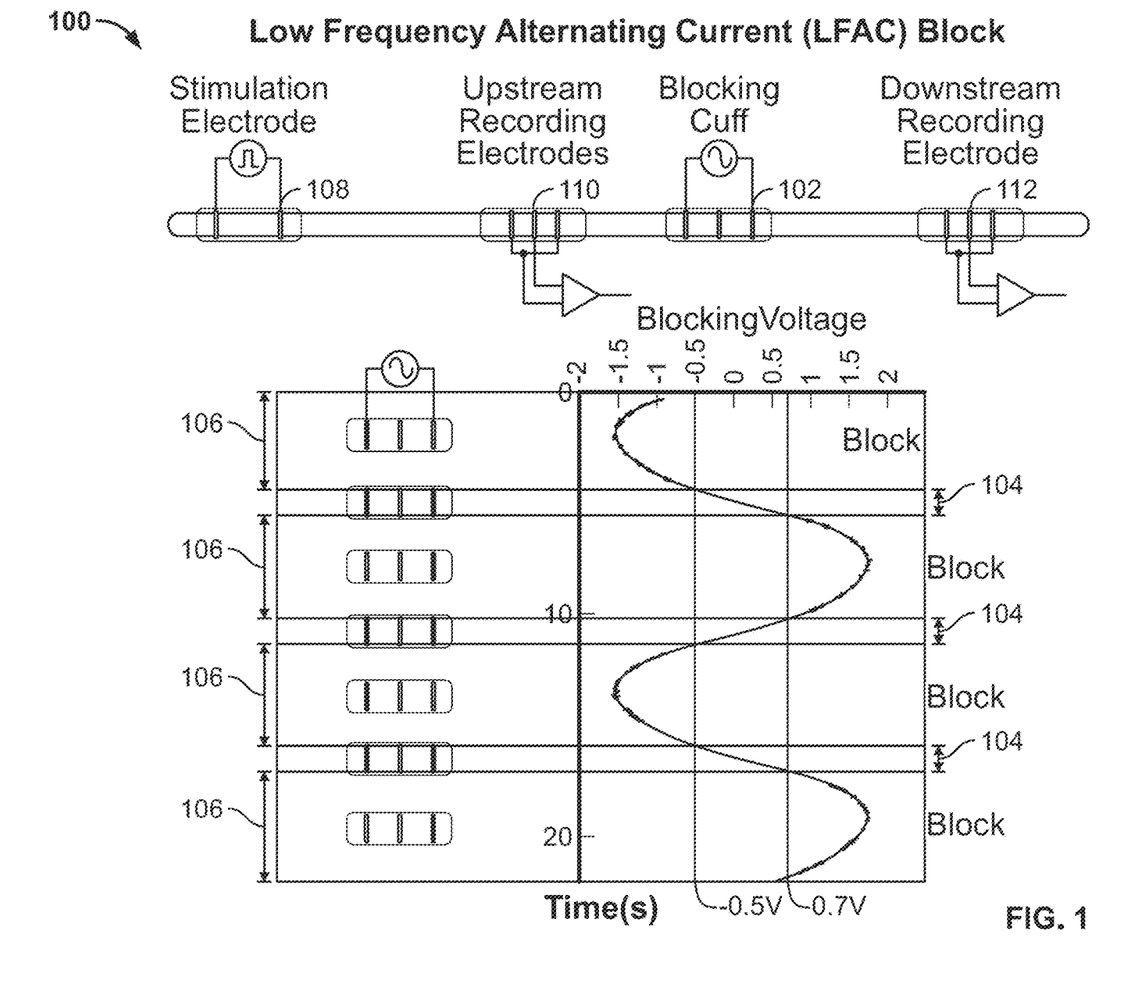
FIG. 1 is a schematic diagram of a low frequency alternating current blocking system in accordance with one embodiment of the present disclosure.

Referring now to FIG. 1, the present disclosure describes a novel means to effect blocking of nerve activity propagating in nerve fibers. A system and method, titled as "Low Frequency Alternating Current" (LFAC) block is generally designated 100, and involves the use of a low frequency alternating blocking current/voltage delivered to a bipolar or multipolar nerve electrode. In one example, the system 100 is demonstrated on earthworm nerve cord and ex-vivo canine vagus nerves. In one example, a blocking waveform is altered in pilot demonstrations, which indicate that frequency and amplitude can have a selective effect on different fiber types. There is some indication that periods of the block are selective to smaller fibers, while other periods are selective to larger fibers. Thus, there is an indication of a possibility of tuning the stimulus waveform to effect fiber size selectivity. In this example, an in-silico model of the phenomenon is being constructed to enable informed electrode and waveform designs to effect more efficient blocking and to understand the underlying mechanisms of LFAC block 100.

More specifically, peripheral nerves are major communication pathways that a nervous system uses to send information from a brain/spinal cord to major organs throughout the body. Electrical stimulation of nerves that innervate these organs has been shown to override the signals controlling the organ. There are two modes in which electrical stimulation influence the neural signaling to the organs. One mode is called activation, where the electrical stimulation impulses introduce activity into the nerve. This increased activity translates to a signal communicating "More." The second mode in which electrical stimulation can be used is called "Blocking." In this case, electrical stimulation stops the ongoing activity flowing through the nerve bundle next to the electrode, decreasing the transmission of activity in the nerve and signaling "Less."

Although activation has been described and understood for at least three centuries, blocking at biocompatible current levels has not. Conventional techniques that are known or being investigated include direct current block (DC) or Anodal Block, kilohertz frequency alternating current block (KHFAC) block. The in-silico models are currently suggesting that Anodal and KHFAC block are different than the mechanism for LFAC block. Anodal block is a result of hyperpolarization of the nerve membrane potential. KHFAC block is considered to have a mechanism of open state sodium channel inactivation, which requires the nerve fiber to turn on before it occurs. It can be thought of as a means to extend the refractoriness of the nerve fiber. Slow ramps, and potentially DC block have similar mechanisms to LFAC block. The lowest threshold block can be a closed state sodium channel inactivation. It is a means to quench nerve activity without activation of the sodium channel. There can be a secondary mechanism for block at a higher threshold. At that point, the LFAC waveform causes anodal break activation, which, if phased properly with a second LFAC channel, causes collision block of the nerve. Finally, at very high levels of block stimulus amplitude, the Anodic phase of the waveform causes hyperpolarization block.

However, the DC block is not considered safe for long term use because of toxic Faradic byproducts produced at each electrode used to establish the block. These byproducts are produced by irreversible oxidative-reductive (redox) reactions taking place at each electrode, and not only cause injury to tissues, but also erode the electrode with time. KHFAC involves the use of high frequency (e.g., greater than or equal to 1kHz) alternating current to effect a nerve block. KHFAC blocks are effected with currents on the order of 1 mA. There are a few ways the nerve block can work. First method involves an artificial activation through an electrode and then blocking a portion or the entire artificially activated nerve volley. Second method is to electrically block natural ongoing activity to remove or modulate aberrant nerve activity. Third method can sequence the block in a way to enable direction (one way block/activation) or velocity selective block with or without artificial nerve activation.

In contrast, the present system and method 100 utilize low frequency (e.g., lower than or equal to 250 mHz) alternating currents directed through bipolar nerve cuff electrodes to enable blocking of nerve propagation through the blocking electrode. In one embodiment, the LFAC block phenomenon can extend from several hundred Hz down to the millihertz (mHz). An exemplary range of LFAC block is between 0.01 Hz and 100 Hz or between 10 mHz and 100 Hz. In another embodiment, a practical range of LFAC block is in the 100's of Hz down to 10's of mHz. For example, the models can suggest that 10 Hz is optimal for small fibers. In fact, the frequency can lend itself to fiber size selective block because of the temporal/spatial cable properties of the nerve, which can be a function of a fiber diameter.

In one example, the current levels of LFAC are much lower than KHFAC blocks, and are in the approximately 100 microampere (uA) range well within a water window of the electrode, or the buildup of charge on the electrode that leads to an oxidation/reduction reaction. With this configuration of low frequency and low current, the present system and method 100 significantly reduces or eliminates the harmful effect of erosion on the electrodes in surrounding areas, thereby producing little or no damage to adjacent tissues. A consequence of the slow cycling of the current from one current to another in a bipolar set of electrodes is that the block is effected on each electrode in turn when it is an anode, and there is an intermediate period where the potential at both electrodes is not sufficient to block. Complete block could be effected with a second set of electrodes using the LFAC block waveform, but phased such that the second set would be blocking in the phase where the first set of electrodes are not blocking, and the first set of electrodes are blocking in the phase where the second set is not blocking.

Another feature of LFAC block 100 is that the blocking waveform is at a frequency outside of the recording bandwidth of nerve activity. In standard stimulation, the release points of DC block and KHFAC block generate significant stimulus artifacts in cases where bioelectric activity is being monitored (recorded) during stimulation. Since LFAC block 100 is out of band with nerve or muscle activity, there is essentially no artifact and activity can be easily monitored during the use of LFAC block 100.

FIG. 1 shows an exemplary design used to test the LFAC block system 100 in both an earthworm and ex-vivo canine vagus nerve preparation. In this example, the mechanism for LFAC block 100 is similar to DC or anodal block. The mechanism of the block 100 passes current through the electrode results in the local hyperpolarization of the transmembrane potential at the Anode, increasing the threshold of activation beyond what is possible through the potentials generated by the propagating action potential. This extinguishes propagating action potential as a function of the length constant of the nerve fiber and the accommodation rate of the fiber's membrane. It is advantageous that unlike DC block, the currents of LFAC block 100 are cycled to reverse the reactions taking place at the electrode and recapture byproducts, thus LFAC block 100 is advantageously biocompatible and compatible for long term use.

In one embodiment, there are two mechanisms for LFAC block 100, namely a closed state sodium channel inactivation block and a hyperpolarization block. A parameter envelope including, but not limited to, frequency, amplitude, phasing vs. fiber diameter and type information associated with LFAC block 100, can be used for operation of LFAC block 100. For example, the inactivation and/or hyperpolarization mechanisms can be used to operate LFAC block 100 along with the parameter envelope. Such inactivation and/or hyperpolarization mechanisms can be used for in-silico, ex-vivo, or in-vivo models of the phenomenon to effect more efficient blocking.

In FIG. 1, at least one blocking cuff electrode 102 along with a blocking stimulus is shown. During zero crossing portions, blocking cuff electrode 102 allows the action potentials to pass until (green zone 104—non-blocking) the blocking waveform reaches a certain threshold range (e.g., as shown in FIG. 1, greater than 0.7 volt (V) or less than −0.5 volt (V)), above which the propagating nerve activity is blocked (red zone 106—blocked). However, the threshold range may vary depending on types of electrodes used or blocking tissues (e.g., fatty nerves). Addition of another pair of contacts and using a second LFAC waveform phased to block during the non-blocking phase of the first electrode pair should enable complete block of the nerve.

In FIG. 1, a stimulation (activation) electrode 108 is used further upstream than the upstream recording electrode to generate a propagating nerve volley going from upstream recording electrode to the downstream recording electrode. Upstream electrodes 110 monitor the nerve volley upstream of blocking cuff electrode 102. A second set of monitoring electrodes 112 are placed downstream of blocking cuff electrode 102 to monitor whether the volley has propagated through blocking electrode 102 or whether it was blocked. A LFAC blocking waveform is presented to contacts of a bipolar cuff electrode. The bottom portion of FIG. 1 shows which contact of the blocking electrode is blocking and which is facilitating, in response to the phase of the LFAC blocking waveform. Near the zero crossing, neither electrode contact presents a potential to effect blocking, thus enabling propagation of the nerve activity through the blocking cuff.

In the illustrated embodiment, LFAC block system 100 is used to demonstrate that the block occurred. In this example, the nerve activity is initiated through first electrode 108 to experimentally model nerve activity traveling down the nerve. Second electrode 102 (conditioning or blocking electrode) would either block or not block the action potential. If the block is demonstrated, a third electrode (e.g., the recording electrode 112) disposed downstream of second electrode 102 cannot see the nerve activity generated with first electrode 108. In one embodiment, this configuration can be used as a therapy.

Other suitable configurations of LFAC block system 100 are also contemplated. For example, in another embodiment, the block can be applied open loop either continuously or with an on/off duty cycle. Another possibility is to have an on-demand block, in which case, the ongoing activity or symptom is monitored, and the block is turned on when needed.

In one example, this technique is tested in an earthworm nerve cord preparation, and the tissue used is an earthworm. Earthworms contain two "giant" nerve fibers, a medial fiber and a lateral fiber. The medial fiber has a diameter that is roughly double that of the lateral fiber, and thus has a conduction velocity that is roughly two times the velocity of the lateral fiber. All of the difficulties and non-linearlities involved with in-vivo nerve stimulation and recording are present with the earthworm, and thus the earthworm is an ideal platform for testing. The earthworm represents a large peripheral nerve trunk with two nerve fibers.

In another embodiment, multiple LFAC sites and sequence/phase the stimulation can be utilized so that complete block can be achieved, or activity of a specific conduction velocity is passed while all other conduction velocities are blocked. In one example, the selective passing of a specific conduction velocity can be in one (anterograde or retrograde) or both directions depending on how the pass phase of the LFAC sites are sequenced. For example, if the two sites are spaced by 100 mm, and the pass phase of LFAC1 leads the pass phase of LFAC2 by 10 ms, the two sites will pass conduction of fibers that have conduction velocities of 10 m/s (100 mm/10 ms) going in the direction of LFAC1 to LFAC2. Other velocities would be blocked. In yet another embodiment, the blocking cuff 102 shown in FIG. 1 can be configured with an amplifier so that the potential or current can be monitored at each of the contacts. This configuration provides a cyclic voltammetry to monitor whether toxic reactions are taking place during LFAC stimulation.

Figure 2:
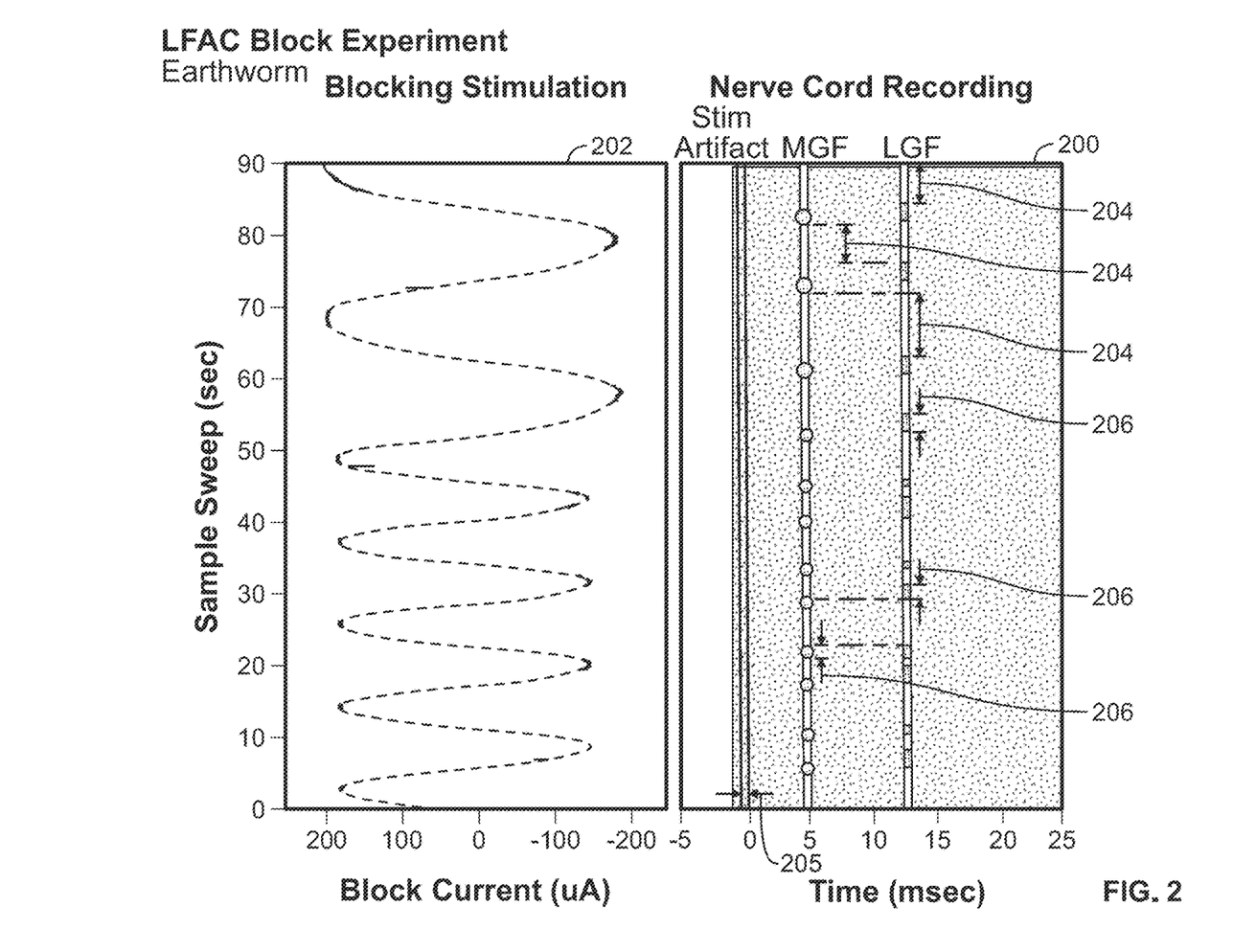
FIG. 2 is a pictorial representation of an exemplary data of the blocking system of FIG. 1 in accordance with one embodiment of the present disclosure.

Referring now to FIG. 2, the system 100 described above is tested using the earthworm as a peripheral nerve analog. FIG. 2 illustrates an exemplary experiment in an earthworm preparation. The earthworm preparation resolves how LFAC affects nerve fibers on a fiber by fiber basis. The earthworm has two giant nerve fibers that have different conduction velocities, which can be monitored how the block affects slower and faster fibers in the earthworm independently.

A left panel 202 shows blocking stimulus and a right panel 200 shows the stimulus triggered downstream recording. In the downstream recording, a red band 204 is shown where the MGF and LGF are blocked. The results of the experiment are shown in FIG. 2. On the right panel 200 of this figure, recording sweeps from continuously acquired signal from the downstream electrode 112 are extracted and plotted as a function of time. Each line represents a 25 millisecond (ms) extraction of the continuous data, aligned to the time when the stimulation (activation) pulse was delivered. A deflection 205 represents the stimulus artifact (e.g., turned on and off using a 0-5 volt range) picked up by the downstream electrode 112. The time increment at 5 ms indicates the time where the deflection resulting from the faster fiber (LGF—Lateral giant fiber) arrives at the downstream electrode and is either detected or missing. The time increment at 13 ms indicates the time where the deflection resulting from the detection of the slower fiber (MGF—Median giant fiber) occurs. Depending on the phase and magnitude of the blocking stimulus waveform shown in a left panel 202, one can see that there are periods where both the MGF and LGF are blocked (periods marked in red 204), as in the first few sweeps of the recording, and periods where the MGF and/or LGF propagate and are detected (deflections marked in green 206). Interestingly, there are periods where the slower fiber (MGF) is blocked while conduction of the faster fiber (LGF) is not and vise-versa.

Figure 3:
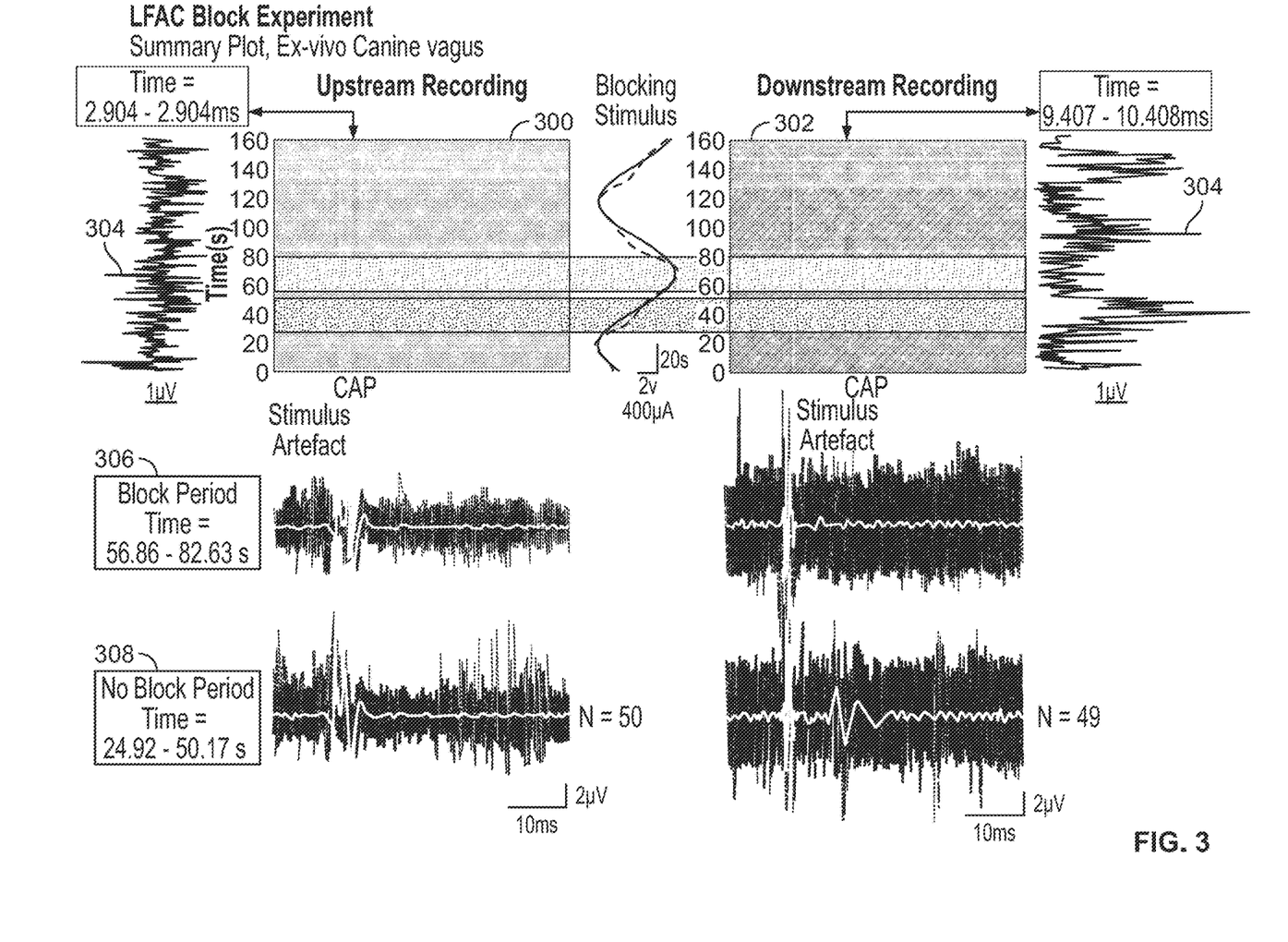
FIG. 3 is a pictorial representation of another exemplary data of the blocking system of FIG. 1 in accordance with one embodiment of the present disclosure.

Referring now to FIG. 3, exemplary data resulting from the blocking system 100 is shown. In this example, the work on the ex-vivo dog vagus nerve shows crossover of the technique to mammalian nerves. In this case, there are hundreds of nerve fibers and it is difficult to resolve the effect on a fiber to fiber basis. But, the effect on electrically activated mass nerve activity can be seen by monitoring the various peaks of the compound action potential (CAP).

More specifically, upstream recording 300 on the left shows a steady and constant compound action potential (CAP) while downstream recording 302 has a CAP that is altered by the blocking cuff stimulation. On the far left and far right the blue waveforms 304 show an absolute averaged waveform on the maximum point of the CAP for the upstream and downstream recordings, respectively. The bottom waveforms show the CAP for both the upstream and downstream recordings for blocking periods 306 and no block periods 308.

In this example, moving from the earthworm to the ex vivo canine vagus nerve, the same system 100 is used as described in FIG. 1. The vagus nerves is excised from freshly euthanized canines and placed in the test setup as described earlier. The canine nerve is used to establish that the LFAC block effect seen in the earthworm translated to mammalian nerves. The results are shown in FIG. 3. Unlike the earthworm, the canine vagus contains hundreds of nerve fibers of various diameters (conduction velocities) and types (myelinated and unmyelinated). Stimulation of the nerve for suprathreshold activation, results in a compound action potential volley that disperses with distance into the various peaks associated with nerve fibers of differing conduction velocities. Thus, the data shown in FIG. 3, unlike the two single unit deflections seen in the earthworm data, displays the presence or lack of presence of the compound action potential.

Upstream electrode 110 detects a consistent compound action potential (CAP) occurring between 2.9 and 3.9 ms post stimulus, while downstream electrode 112 detects a dispersed CAP that occurs only during phases of the blocking waveform where the waveform is near zero. The experiment demonstrates that LFAC block 100 can be effected in the mammalian nerve.

Figure 4:
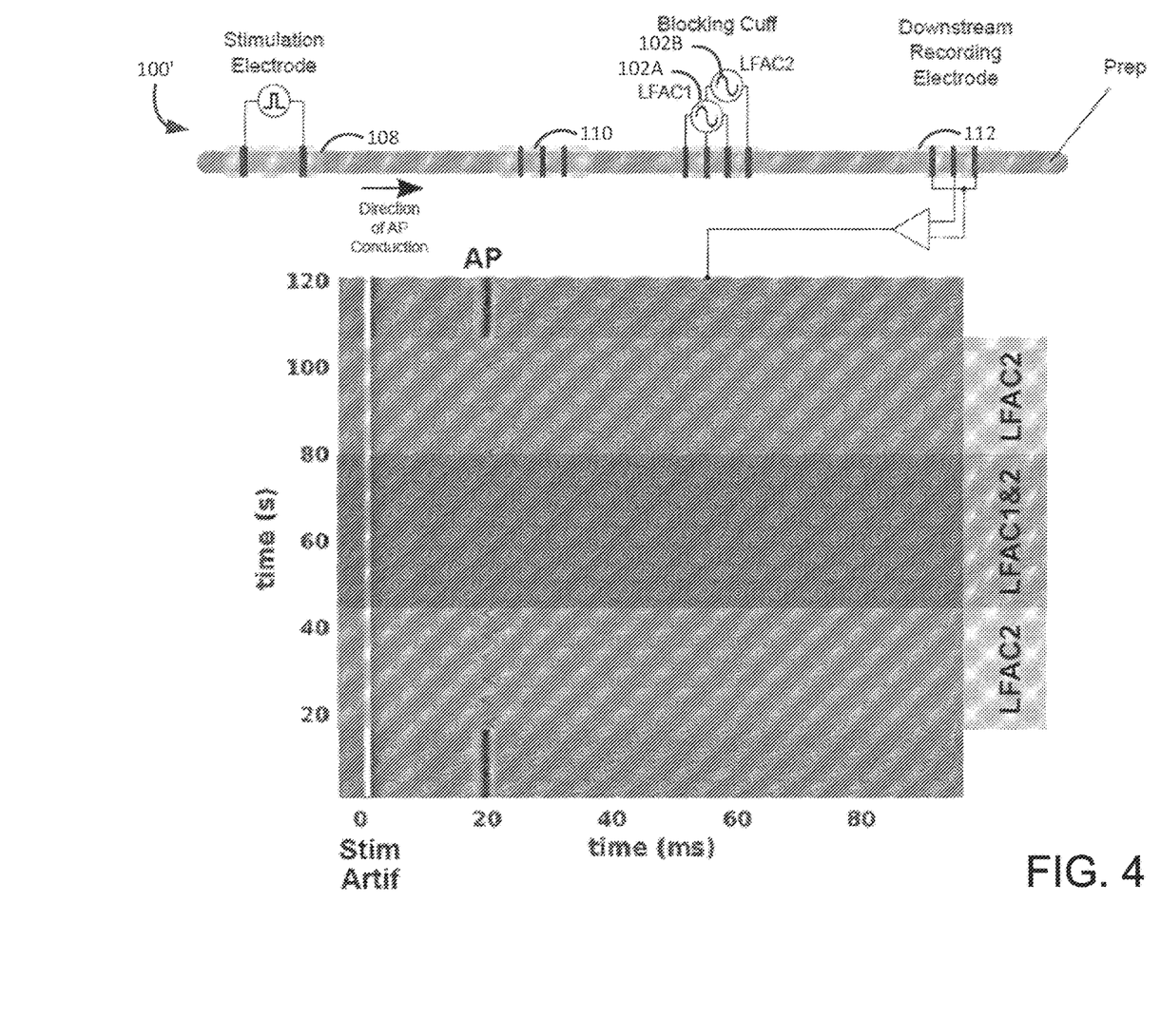
FIG. 4 is a schematic diagram of a low frequency alternating current blocking system in accordance with another embodiment of the present disclosure.

FIG. 4 shows another exemplary design used to test LFAC block system 100' using at least two blocking electrodes 102A and 102B. In this configuration, a full block is achieved by using two LFAC channels LFAC1 102A and LFAC2 102B that are selectively phased so that a no-block phase of one channel 102A is a block phase of the second channel 102B. As a result, the electrical signal (e.g., action potential AP) generated by first electrode 108 is completely blocked in the LFAC1&2 time region, thereby preventing it from propagating through the nerve system.

Figure 5:
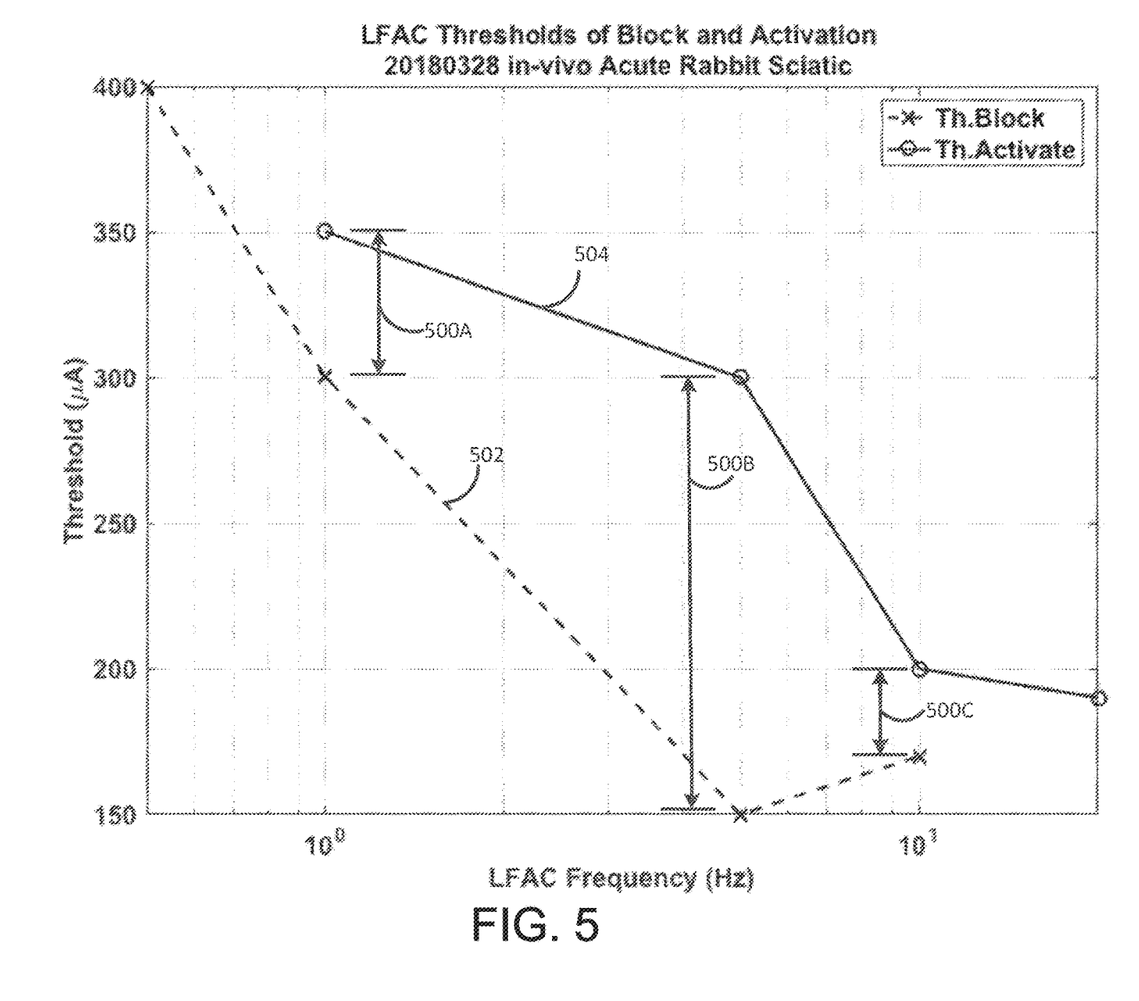
FIG. 5 is a graphical representation of an exemplary data of the blocking system featuring a block signal and a nerve activation signal.

FIG. 5 shows exemplary results from an experiment illustrating that there is frequency dependence to the thresholds of block and activation, as well as evidence showing that there is a window 500A, 500B, 500C (collectively 500) of block without activation. Each window 500A, 500B, 500C represents a gap between a block threshold 502 and an activation threshold 504, during which a successful block can occur without the nerve activation propagating the action potential. In this exemplary plot, an X-axis is shown in a logarithmic-linear scale representing LFAC frequency, and a Y-axis is shown in a linear plot representing threshold current. For example, for X-axis, $10^0$ represents an integer value of 1 and $10^1$ represents an integer value of 10.

Figure 6:
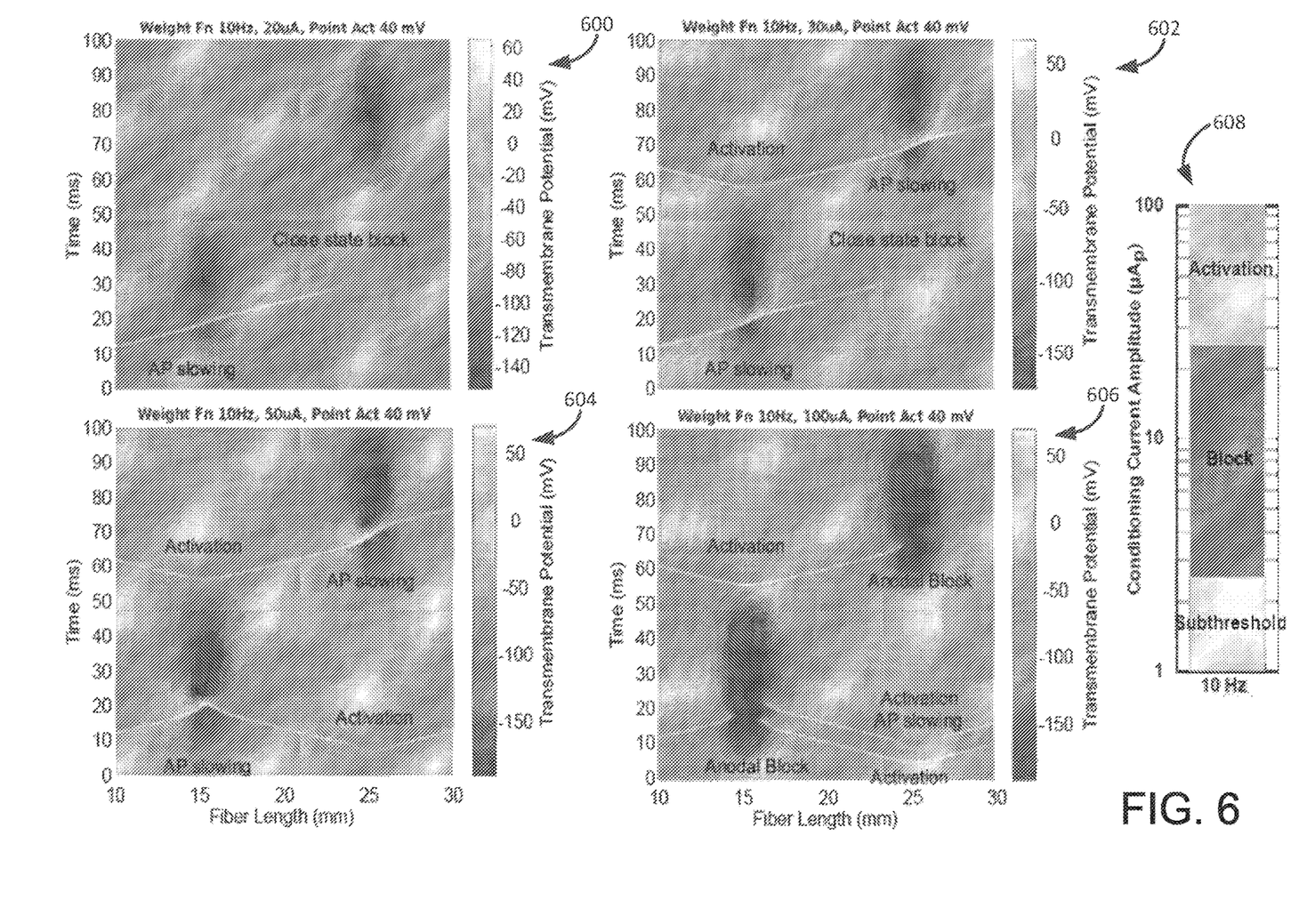
FIG. 6 is a pictorial representation of yet another exemplary data of the blocking system of FIG. 1 in accordance with one embodiment of the present disclosure.

FIG. 6 shows exemplary in-silico simulations of LFAC block system 100 and/or 100' at 10 Hz and various types of blocks and activations that occur with increasing block stimulation amplitude. In this example, there is a window during which the closed state sodium channel inactivation occurs without the nerve activation. For example, in a first graphical representation 600, the action potential AP is successfully blocked without the nerve activation at a location of approximately 23 millimeter in the sample nerve fiber when using a current level of 20 microampere. However, as shown in the other graphical representations 602, 604, 606, the nerve activation occurs when using the current level at 30, 50, or 100 microampere. Thus, as illustrated in a bar graph 608 shown in a logarithmic-linear scale, exemplary conditioning current amplitude for successful blocking without the nerve activation can range between 2.5 and 25 microampere to avoid the unwanted nerve activation. The subthreshold represents another window where no blocking occurs. In further embodiments, LFAC block 100 can be used to demonstrate the concept in-vivo in an anaesthetized animal, and to model/describe in-silico the biophysics demonstrated by FIGS. 2-6. Furthermore, while the above description describes hardware in the form of a processor executing code, hardware in the form of a state machine, or dedicated logic capable of producing the same effect, other structures are also contemplated.

While this present disclosure has been described as having an exemplary design, the present disclosure may be further modified within the spirit and scope of this disclosure. This application is therefore intended to cover any variations, uses, or adaptations of the present disclosure using its general principles. Further, this application is intended to cover such departures from the present disclosure as come within known or customary practice in the art to which this present disclosure pertains.

What is claimed is:

1. A nerve activity blocking system, comprising:
   first and second electrodes;
   a blocking signal generator configured to generate a first blocking electrical signal coupled to the first and second electrodes, wherein the first blocking electrical signal is a sinusoidal low frequency alternating current signal having a frequency between 0.01 Hz and 100 Hz defining alternating positive voltage components and negative voltage components;
   wherein the positive voltage components and the negative voltage components have peak voltage levels greater than non-zero threshold voltage levels defining blocking zones that cause the blocking electrical signal to prevent propagation of action potentials by overriding another electrical signal controlling an organ of the body, and wherein voltages of the positive voltage components and the negative voltage components less than the non-zero threshold voltage levels define non-blocking zones allowing propagation of the action potentials.

2. The system of claim 1, wherein a current level of the low frequency alternating current is approximately 100 microampere.

3. The system of claim 1, wherein at least one of frequency and amplitude of the blocking electrical signal selectively controls an effect of the blocking based on a fiber type of the nerve system.

4. The system of claim 1, further comprising a first recording electrode disposed upstream of the first and second electrodes, and configured to monitor the action potential propagating through the nerve system.

5. The system of claim 1, further comprising a second recording electrode disposed downstream of the first and second electrodes, and configured to monitor an extent of blocking of the action potential by the blocking electrical signal.

6. The system of claim 1, further comprising third and fourth blocking electrodes coupled to a blocking signal generator configured to generate a second blocking electrical signal that causes a complete block of the action potential by phasing the second blocking electrical signal with the first blocking electrical signal.

7. A method of blocking a nerve activity in a body, comprising:
   generating, using a blocking signal generator, a first blocking electrical signal that blocks, at least in part, an action potential propagating through a nerve system of the body using a low frequency alternating current; and
   applying the first blocking electrical signal to the body through first and second electrodes;
   preventing, using the first blocking electrical signal, propagation of the action potential by overriding another electrical signal controlling an organ of the body; and
   wherein the first blocking electrical signal is a sinusoidal low frequency alternating current signal having a frequency between 0.01 Hz and 100 Hz defining alternating positive voltage components and negative voltage components, and wherein the positive voltage components and the negative voltage components have peak voltage levels greater than non-zero threshold voltage levels defining blocking zones that cause the blocking electrical signal to prevent propagation of action potentials, and wherein voltages of the positive voltage components and the negative voltage components less than the non-zero threshold voltage levels define non-blocking zones allowing propagation of the action potentials.

8. The method of claim 7, further comprising setting a current level of the low frequency alternating current at approximately 100 microampere.

9. The method of claim 7, further comprising selectively controlling an effect of the blocking based on a fiber type of the nerve system based on at least one of frequency and amplitude of the blocking electrical signal.

10. The method of claim 7, further comprising:
    disposing a first recording electrode upstream of the first and second electrodes; and
    monitoring the action potential propagating through the nerve system using the first recording electrode.

11. The method of claim 7, further comprising:
    disposing a second recording electrode downstream of the first and second electrodes; and
    monitoring an extent of blocking of the action potential by the blocking electrical signal using the second recording electrode.

12. The method of claim 7, further comprising generating a second blocking electrical signal and applying the second blocking electrical signal to the body using third and fourth electrodes, wherein the second blocking electrical signal causes a complete block of the action potential by phasing the electrical second signal with the first blocking electrical signal.

\* \* \* \* \*